United States Patent [19]

Prahl

[11] 4,426,742
[45] Jan. 24, 1984

[54] BREAST PROSTHESIS

[75] Inventor: Jan Prahl, Rullstorf, Fed. Rep. of Germany

[73] Assignee: Beiersdorf Aktiengesellschaft, Hamburg, Fed. Rep. of Germany

[21] Appl. No.: 326,272

[22] Filed: Dec. 1, 1981

[30] Foreign Application Priority Data

Dec. 12, 1980 [DE] Fed. Rep. of Germany ....... 3046784
Dec. 12, 1980 [DE] Fed. Rep. of Germany ....... 3046785
Dec. 12, 1980 [DE] Fed. Rep. of Germany ....... 3046786

[51] Int. Cl.$^3$ .......................... A41C 3/10; A61F 1/00
[52] U.S. Cl. ........................................... 3/36; 128/505
[58] Field of Search ...................... 3/36; 128/462, 463, 128/478-481, 505

[56] References Cited

U.S. PATENT DOCUMENTS

| 2,633,440 | 3/1953 | Scholl | 128/505 X |
| 2,851,692 | 9/1958 | Livingston et al. | 3/36 X |
| 3,301,254 | 1/1967 | Schickedanz | 3/36 X |
| 4,125,117 | 11/1978 | Lee | 128/481 |

FOREIGN PATENT DOCUMENTS

| 2742394 | 3/1979 | Fed. Rep. of Germany | 3/36 |
| 2,451,738 | 11/1980 | France | 3/36 |

Primary Examiner—Ronald L. Frinks
Attorney, Agent, or Firm—Jordan B. Bierman; Linda Bierman; C. Cornell Remsen, Jr.

[57] ABSTRACT

Breast prosthesis of an elastic plastic, in particular of silicone rubber composition, having a breast molding corresponding to the female breast and having a contact area adapted to the human body form, which carries an adhesive composition for attachment of the breast prosthesis to the body, which is characterized in that the breast molding comprises on the body-contact side, approximately centered, a recess and an adapter type molding retained therein and rotatable about its vertical median axis, the external wall area of which, turned toward the body, is provided with a coating of an adhesive composition tolerated by the skin. Optionally the breast molding comprises in its upper region a soft core which is highly flexible relative to the cup material.

12 Claims, 5 Drawing Figures

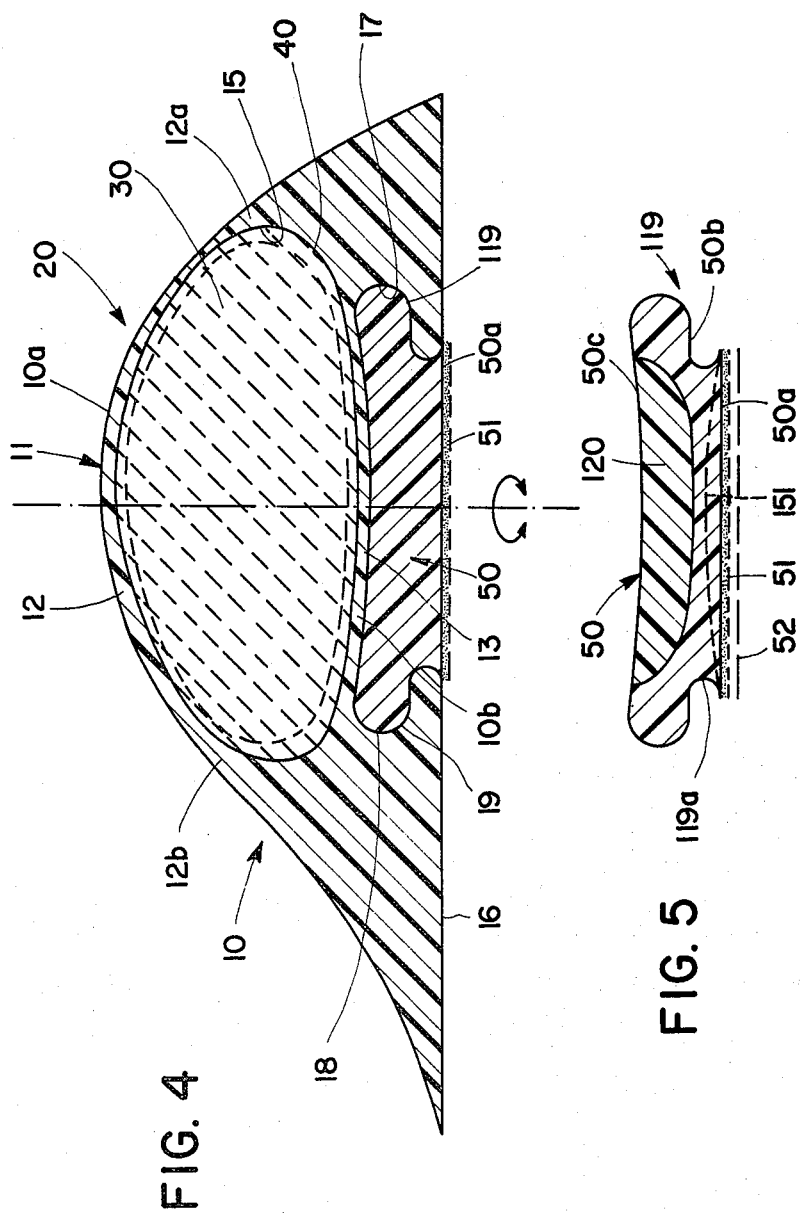

BREAST PROSTHESIS

The invention relates to a breast prosthesis of an elastic plastic, in particular of silicone rubber composition, having a breast molding corresponding to the form of the female breast and having a bearing surface adapted to the human body form and on which an adhesive is applied for attachment of the breast prosthesis to the body.

The number of breast-amputated women shows an increasing tendency, the amputation being usually the consequence of malignant tumors. Depending on the size of the spread of the tumor, scars of variable size and often poorly covered body areas result from the amputation. The scars forming after amputation are hypersensitive to pressure edges and chafing areas. An additional factor is that due to the breast amputation the symmetrical weight distribution on the spinal column is disturbed, so that a breast prosthesis must meet the following basic requirements: The prosthesis must be largely adapted to the body form and must form on the body contact side a largely closed contact area; the weight determination of the breast prosthesis must be chosen so that as to weight mass it corresponds to the other usually intact breast, avoiding especially alterations of the shoulder girdle and of the spinal column; the volume of the breast prosthesis should be such that in its swing behavior it comes very close to the natural breast, and moreover the surface of such breast prostheses should consist of physiologically harmless material, since often open scars are to be found.

Known is a breast prosthesis consisting of a flexible, one-piece, air-free, shell type element simulating the breast form (DE-GM No. 7 603 424). In this known breast prosthesis the breast element consists of addition-polymerizing two-component silicone rubber, the top and bottom sides of which are covered by a plastic foil, these foils being welded together along the edge of the shell type element. By the use of a breast prosthesis element of addition-polymerizing two-component silicone rubber one attempts to achieves a prosthesis which shows, during movements of its wearer, the natural appearance, the mobility and softness of a sound breast and is pleasant to wear and easy to put on. Such breast prostheses, provided with a cavity in the contact side region, are made in shell form, but they do not fulfill the essential requirements for a breast prosthesis. Above all, the problems of the contact area are insufficiently solved and the vertical swing equalizations, of importance especially for larger breast forms, are not obtained.

Further a breast prosthesis is known having a flexible, one-piece hollow body simulating the breast form which is filled air-free with a liquid and which is formed as a double-walled shell simulating the external form of the breast (US-PS No. 2,543,499). Such air-free, liquid-filled, bag type structures are heavier than the normal breast and are rejected as unnatural because of their hanging appearance. Another disadvantage of the liquid-filled prosthesis is that the filling materials may migrate out and flow out if the surrounding envelope is damaged.

Still another breast prosthesis with liquid filling has become known, which consists of an outer envelope, made of elastic and porous material, preferably latex foam or plastic foam. This envelope is provided with a hollow insert of impermeable, supple, in particular thin-walled material, which is expediently adapted in its form to the interior of the outer envelope and is filled more or less, as required, with the liquid which serves at the same time as weighting material. By the combination of an outer envelope of soft foam with a specially adapted liquid-filled insert, it is to be possible easily to match the form of the outer envelope and of the insert and the liquid quantities to each other in such a way that with regard to its form, elasticity, flexibility under pressure and mobility even under the influence of gravity the prosthesis is virtually equivalent to the natural breast. Apart from the above discussed disadvantages in liquid-filled breast prostheses, this known prosthesis has the additional disadvantage, however, that with a partial filling of the insert with liquid, the swing behavior of such a prosthesis is impaired, so that it offers the wearer no advantages but only disadvantages, in that a partially liquid-filled breast prosthesis in no way corresponds to the swing behavior of the natural breast. Besides, a partial filling of such a prosthesis may cause secondary shaking noises, so that in the end result such a breast prosthesis in no way corresponds to the natural breast as to form and behavior. Moreover, if such a prosthesis is partially filled with liquid, the remaining cavity must be sealed off, to avoid excessive liquid movement inside the insert (DE-GM No. 17 28 134).

Another known breast prosthesis consists either of an element made of elastic and spongy material or of a hollow body of light, fine-pore material with a filling of elastic and spongy material (US-PS No. 2,851,692). In the interior of the breast prosthesis element cylindrical cavities are provided which contain movable weights. Such prostheses, however, are too solid to have the appearance of a natural breast.

Known also are breast prostheses consisting of a foam molding (DE-PS No. 13 03 139). This foam molding, which has flat regions, is surrounded in spaced relation by a shell type, double-walled hollow body of plastic which is joined to the molding only along its edge and is filled with a liquid. This breast prosthesis has the same disadvantage as all liquid-filled breast prostheses. Moreover, it is very complicated in its construction; and it does not meet all requirements of a natural appearance.

Further there has become known a breast prosthesis made by molding, intended to be placed or inserted in a brassiere product, made of soft-elastic, porous, adhering, skin color plastic, as e.g. accelerator-polymerized soft silicone rubber, which consists of a forwardly arched hollow central part whose convex exterior has the form of a female breast with nipple and areola and whose concave interior is arched in bosom form maintaining the desired prosthesis wall thickness and which, concentric with the nipple, has a bore as well as thin flexible marginal spurs surrounding this central part, of which the axillary marginal spur is prolonged in an extension whose length and width are dimensioned so that with it the axillary lymph gland region can be covered when the prosthesis is in place, whereby a breast prosthesis approaching the appearance and elastic properties of the natural breast is said to be created, which does not adversely affect the skin and adheres well thereon and hence does not slip, is moreover light and airy when worn and fits into the common brassiere products and in addition can be produced in quantity and hence at low cost (DE-GM No. 76 31 795).

Furthermore there has become known a breast prosthesis for women having a main part simulating the actual mammary gland and an auxiliary part contiguous thereto on one side to creat a continuous transition between the prostheses and the wearer's body in the vicinity of the armpit, the main part and auxiliary part being formed by an elastic medium surrounded by an envelope, where the elastic medium is an addition-polymerizing silicone rubber and the envelope is formed by a thermoplastic linear polymerization, high-strength polyurethane foil (DE-GM No. 76 02 166). By a prosthesis so designed, the danger of rapid outflow of the elastic shaping medium otherwise occurring with liquid-filled breast prostheses when the prosthesis element is damaged can be avoided by choosing a silicone filling instead of the liquid.

These known breast prostheses fulfill approximately the basic requirements for breast prostheses, but with respect to their design and the materials used they are not such that to the touch differences from the natural breast are no longer perceptible. The requirement that when touching a breast prosthesis no differences from the natural breast are perceptible and noticeable is thus not fulfilled by the known breast prostheses.

Moreover, the known breast prostheses convey to their wearer while wearing the prosthesis inside a bra the feeling of having a natural breast. But the wearer of such a breast prosthesis feels a particularly adverse effect when the bra must be taken off and hence the prosthesis removed with it.

To eliminate this disadvantage, a breast prosthesis of plastic material which simulates the natural female breast quite realistically has become known which is provided with adhesive fasteners by means of which the prosthesis can be affixed on the skin of the human body, so that such a prosthesis can remain joined to the body over protracted periods and need not be taken off even when washing, bathing or during similar activities. As the adhesives used in these known breast prostheses are not reusable indefinitely after detachment, the adhesive fasteners on this prosthesis are expediently made to be exchangeable. What is disadvantageous in this known breast prosthesis is, however, that after it has been attached to the skin, the fit can be corrected only if the prosthesis is taken off, brought into the correct fitting position, and then reattached. The life of the adhesive properties of the adhesives used is thereby substantially shortened (DE-OS No. 27 42 394).

In contradistinction, it is the object of the present invention to create a breast prosthesis with a body-contact-side adhesive area which permits a rotational correction also after attachment to the skin of the human body, so that the correct fitting position of the breast prosthesis can be adjusted afterwards.

For the solution of this problem a breast prosthesis of the above-described kind is proposed which according to the invention is designed in such a way that its cup comprises toward the body, approximately centered, a recess and an adapter type molding retained therein. The cup is rotatable about its vertical median axis and the external wall area of the molding, turned toward the body, is provided with a coating of an adhesive composition tolerated by the skin.

By the realization of a breast prosthesis with a glue-on adapter about which the cup is rotatably mounted, it becomes possible for the wearer of such a breast prosthesis to effect a rotational correction of the prosthesis after the prosthesis as a whole has been attached to the skin of the body, to thereby bring the prosthesis into the correct fitting position, and thus also to adapt it to the respective brassiere product used. Because only the adapter type molding carries the adhesive on the outside, the prosthesis adheres on the skin only in the region of the rotatable molding, and not over the entire contact area, thereby making it possible to effect a rotational correction on the breast prosthesis at any time.

The objects of the invention are illustrated by the examples in the drawings, in which:

FIG. 4 is a vertical section through the breast prosthesis of FIG. 3 showing the molding about which the cup may be rotated; and FIG. 5 shows a vertical section through a modified form of molding which is attached to the breast.

Figure 1:
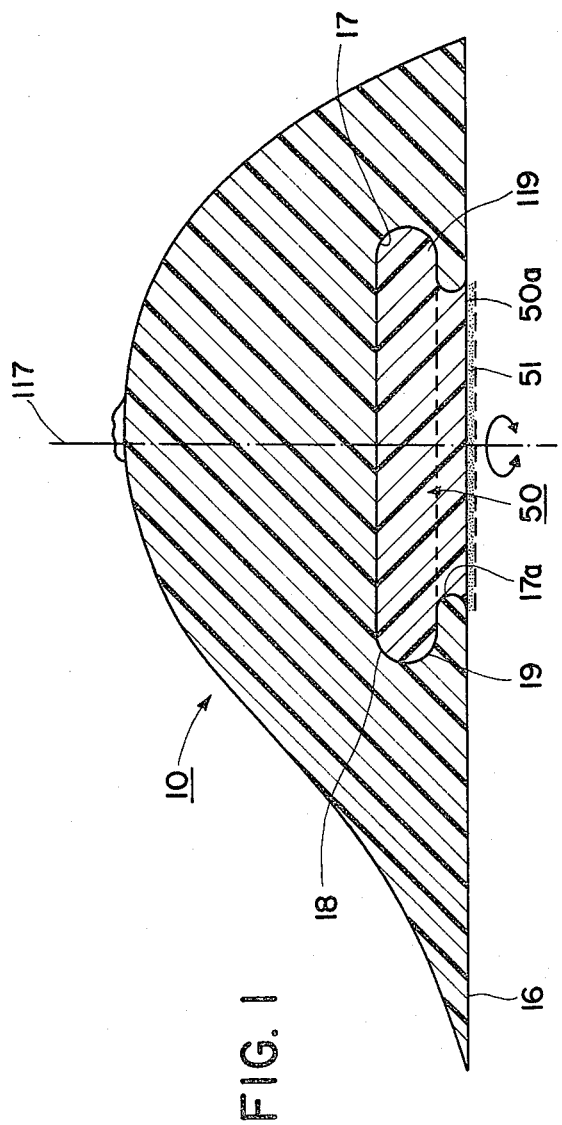
FIG. 1 shows a breast prosthesis with an adapter type molding rotabably retained in the cup, having an external coating of an adhesive composition, in vertical section.

In the form of realization of a breast prosthesis shown in FIG. 1, the cup or breast molding thereof is marked 10, and has a form corresponding to the female breast and may be solid or hollow. The cup 10 preferably consists of an elastic, homogeneous plastic, in particular a toxicologically unobjectionable, addition-polymerized silicone rubber; more particularly there may be used also soft silicones obtained by cross-linkage control which are not, as known, adjusted in their flexibility by oil additions. The contact area of the cup is indicated at 16.

In the region of its contact area 16 the cup 10 has approximately centered recess 17, which is designed to receive and retain an adapter type molding 50. The cup 10 is rotatable on said molding about its vertical median axis 117, and the external wall area 50a of the molding, lying in the plane of the contact area 16 of the cup, is provided with a coating 51 having adhesive composition tolerated by the skin.

The recess 17 is generally cylindrical and has a circular crosssection. The adapter type molding 50 has circular disk form and consists advantageously of the same material of which the cup 10 of the breast prosthesis is made. Alternatively the adapter type molding 50 may be made of a different material, but it is essential to use materials having a certain flexibility and adaptability to the body.

As adhesive composition for the coating 51 on the outer wall 50a of the adapter type molding 50, all those adhesive compositions which are toxicologically unobjectionable may be used. If the cup 10 is made of an addition-polymerized silicone rubber, then the glue area of the molding 50 toward the body of the wearer of the prosthesis is preferably derived from the same rubber composition as adhesive composition. During vulcanization the adhesive composition and the adapter type molding 50 coalesce.

To ensure the relative rotatability of the adapter type molding 50 and cup 10, the recess 17 is provided on its inner wall area 17a with an annular guide profile 19, into which engages a counter-profile 119 integrally formed on the peripheral wall 50b of the disk-shaped molding 50 is retained.

In the embodiment shown in FIG. 1, the recess 17 is formed by an annular wall section 17a, which changes over into the contact area 16 of cup 10 and which is contiguous to an annular groove type section 18. At its peripheral wall 50b the adapter type molding 50 presents as counter-profile 119 a profile 119a engaging in the guide profile 19 formed by the annular wall section 17a and the annular groove type section 18 as above described, so that due to its design the adapter type molding 50 is retained within the recess 17. An adapter type molding 50 thus designed can be inserted into the recess 17 without effort. Due to the circular disk form of molding 50, a rotational correction of the breast prosthesis after attachment of the prosthesis to the skin of the person wearing the prosthesis is thus possible.

When the adhesivity of the molding 50 diminishes, a new molding 50 with adhesivity is insertable in the recess 17 of the existing breast prosthesis without effort.

If cup 10 is formed as a hollow body, it has in the region of its contact area 16 a neck-like constriction which extends into the interior of the hollow cup and which may be provided with support ribs to maintain a certain form stability of the cup. In the inner wall region this neck-like constriction then has the guide profile 19, into which the counter-profile 119 of the adapter type molding 50 can be inserted, thus assuring the free rotational mobility of the breast prosthesis.

Figure 2:
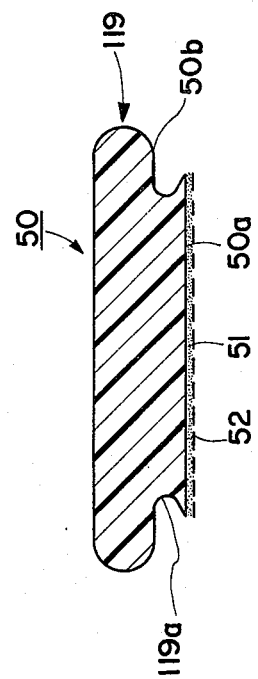
FIG. 2 shows the adapter type molding alone in vertical section.

On the outer wall area 50a of molding 50 the coating 51 is preferably initially covered by a removable protective sheet 52, which is pulled off before the breast prosthesis is applied on the skin (FIG. 2).

It is another object of the present invention to create a breast prosthesis with a body-contact-side adhesion area, whose upper molding does not, despite retention of the breast form, become perceptible on touch to any differences from the natural breast, and in which movement deflections occurring during horizontal and vertical movements of the upper molding cannot be transmitted directly to the adhesion of the prosthesis to the body, and which also after attachment to the skin of the human body permits a rotational correction, so that the correct fitting position of the prosthesis can be adjusted afterward.

For the solution of this problem a breast prosthesis of the initially-described kind is proposed which is characterized according to the invention by the combination of the following features:

(a) The cup has in its upper part, in particular its nipple region, a soft core which is highly flexible relative to the cup material, and (b) on the body-contact side, approximately centered, a recess about which a cup is an adapter type molding retained therein and rotational about its vertical median axis, and in which the external wall area of the molding, turned toward the body, is provided with a coating of an adhesive composition tolerated by the skin.

An embodiment of the invention is proposed in which to form this soft core, the cup has in its upper part, i.e. in particular in its nipple region, an upper wall section formed as a thin skin and in its lower part a lower wall section likewise formed as a thin skin, the two wall sections being joined together with formation of a bladder type closed cavity which is filled with a silicone gel body.

By this embodiment of the invention a breast prosthesis with a soft upper molding has been created, so that on touch no differences from the natural breast are perceptible. Because the gelatinous front portion of the breast prosthesis can execute horizontal and vertical movements, direct transmission of these movement deflections to the body adhesion is avoided.

By the further design of the breast prosthesis with a glue-on adapter rotatably mounted in its molding, the wearer of such a prosthesis is able to effect a rotational correction of the prosthesis after attachment thereof on her skin, to bring the prosthesis into the correct fitting position and thus also to adapt it to the particular brassiere product used. Because only the adapter type molding mounted for relative rotation in the cup carries the adhesive on the outside, the prosthesis adheres on the skin only in the region of the rotatable molding, not over the entire contact area, whereby it is possible to effect a rotational correction on the prosthesis at any time.

Additional advantageous forms of realization will become evident, particularly advantageous being the one where the cup has in the region of its contact area an axial opening opposite the silicone gel body, which can widen to an annular groove type section lying below the silicone gel material in order thereby to permit the silicone gel body to swing with the upper part of the cup. Simultaneously the skin uptake of the cup in the medial portion is thereby arranged so that through increased tensions of a brassiere a pressure deformation into the contact uptake can take place.

Figure 3:
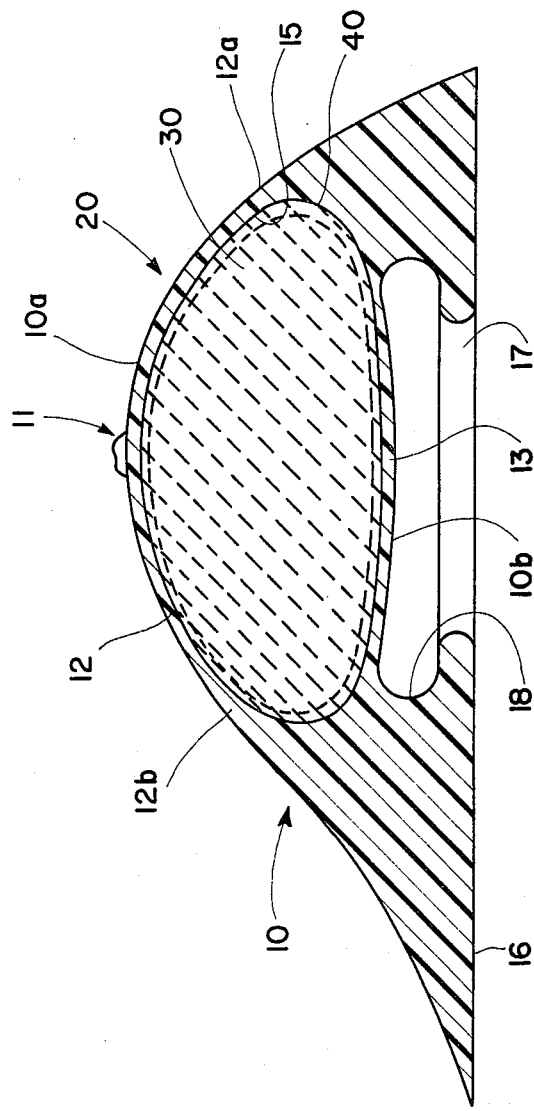
FIG. 3 is a vertical section through a modified form of cup for a breast prosthesis which has a soft core disposed in its upper part.

The breast prosthesis consists according to FIG. 3 of a cup 10 of an elastic homogeneous plastic, in particular a toxicologically unobjectionable addition-polymerized silicone rubber. The upper portion marked 11 is equipped with a nipple and areola in accordance with the female breast. The contact area of cup 10 is indicated at 16. In particular there are used soft silicones obtained by crosslinkage control which are not, as known, adjusted in their flexibility by oil additions.

In the region of its upper part 11, cup 10 has a soft core 20 which is highly flexible relative to the other cup material; it is formed in the upper front portion 10a of cup 10 and extends into the lower portion 10b thereof.

To form this soft core 20, the cup 10 has in its upper front portion 10a a wall section 12 which is formed as a thin skin. This skin type wall section 12 is extended to the central portion of the cup, so that there results a bladder type closed cavity 15 which corresponds to the cup and which is filled with a hypocrosslinked silicone gel body 30. The lateral walls 12a and 12b contiguous to the thin wall section 12 taper conically and uniformly toward the upper part 11 of cup 10, because otherwise an edge formation would result in the outward form of the cup 10. The wall section 13 lying under wall section 12 and limiting in the lower portion 10b the cavity 15 is likewise formed as a thin skin corresponding to wall section 12.

The highly flexible soft part 20 of cup 10 constitutes a satisfactory bearing surface adapted to the body, as it cannot absorb the compressive forces transmitted through a brassiere to the breast prosthesis in a form-stable manner. To this end in particular the lower, supporting breast prosthesis component is made of a higher-crosslinked material.

After introduction into the cavity 15 of cup 10 the silicone-gel body 30 is coalesced with the cavity-limiting wall areas 12,12,15b,13 during the vulcanization process. The introducing of the silicone gel into the cavity 15 can be effected e.g. by means of an opening in wall section 12 closable after completion of the filling process.

To prevent the mass of the silicone gel body 30 from migrating through the thin wall sections 12 and 13, or specifically to avoid that the plasticizer components of the silicone gel body can diffuse through these wall sections, the wall area limiting the cavity 15 is lined with a plastic foil 40 which is plasticizerimpermeable and which prevents a diffusing-through of the sticky silicone gel composition of the body 30. Advantageously one uses as lining foil 40 a polyurethane foil.

In the region of the contact area 16 of cup 10, an axial recess 17 is provided, which widens to an annular groove type section 18 lying below the silicone gel body 30, to facilitate a swinging of the silicone gel body 30 with the upper part of cup 10. The recess 17 is limited in the widened section 18 at the top by the wall section 13 of cup 10.

The cup 10 of the breast prosthesis shown in FIG. 4 is similar to that shown in FIG. 3.

In the region of its contact area 16, the cup 10 has an approximately centered recess 17 which serves to receive and retain an adapter type molding 50 about which the cup is rotatable on its vertical median axis 117, and the external wall area 50a of the molding, lying in the plane of the contact area 16 of the cup, is provided with a coating 51 of an adhesive composition tolerated by the skin.

The recess 17 is generally cylindrical and has a circular crosssection. The adapter type molding 50 has a circular disk form and consists advantageously of the same material of which the cup 10 of the breast prosthesis is made. Alternatively the adapter type molding 50 may be made of a different material, but it is essential to use materials having a certain flexibility and adaptability to the body.

As adhesive composition for the coating 51 on the outer wall 50a of the adapter type molding 50 all those adhesive compositions which are toxicologically unobjectionable may be used. If the cup 10 is made of an addition-crosslinked silicone rubber, then the glue area of the molding 50 toward the body of the wearer of the prosthesis is preferably derived from the same rubber composition as adhesive composition. During vulcanization the adhesive composition and the adapter type molding 50 coalesce.

To ensure relative rotatability between the adapter type molding 50 and cup 10, the recess 17 formed in the latter is provided on its inner wall area 17a with an annular guide profile 19, into which engages a counter-profile 119 integrally formed on the peripheral wall 50b of the disk-shaped molding 50 and is retained in the guide profile 19.

In the embodiment shown in FIG. 4, the recess 17 is formed by an annular wall section, which changes over into the contact area 16 of cup 10 and to which is contiguous an annular groove type section 18. At its peripheral wall 50b the adapter type molding 50 presents as counter-profile 119 a profile 119a engaging in the guide profile 19 formed by the annular wall section and the annular groove type section 18, so that due to its design the adapter type molding 50 is retained in the recess 17. An adapter type molding 50 thus designed can be inserted into the recess 17 without effort. Due to the circular disk form of molding 50, a rotational correction of the breast prosthesis after attachment of the prosthesis to the skin of the person wearing the prosthesis is possible.

When the adhesivity of the molding 50 diminishes, a new molding 50 with adhesivity is insertable in the recess 17 of the existing breast prosthesis without effort.

If cup 10 is formed as a hollow body, it has in the region of its contact area 16 a neck-like constriction which extends into the interior of the hollow cup and which may be provided with support ribs to maintain a certain form stability of the cup. In the inner wall region this neck-like constriction then has the guide profile 19, into which the counter-profile 119 of the adapter type molding 50 can be inserted, thus assuring the free rotational mobility of the breast prosthesis.

On the outer wall area 50a of molding 50 the coating 51 is covered by a removable protective sheet 52, which is pulled off before the breast prosthesis is applied on the skin (FIG. 5).

As FIG. 5 shows, the adapter type molding 50 may have in the region of its upper wall area 50b a soft core 120, which is highly flexible relative to the material of which molding 50 is made. By using this soft core 120 a better hug of the breast prosthesis to the brassiere worn by the wearer of such a breast prosthesis is obtained, for due to this special design of molding 50 it participates in the overall properties of the cup 10 without having a form-stabilizing effect on it. Moreover, the effect achieved with the soft core 20 in cup 10, namely of not letting any differences from the natural breast become perceptible on touch, is in no way impaired, since pressure actions onto the upper part 20 of cup 10 are transmitted through the skin type lower wall sections 13 to the soft core 120 in the adapter type molding 50 and by the latter pressure forces are absorbed, with the result that the pressure forces are transmitted over the contact area 16 of the cup and onto the body skin when the breast prosthesis is worn. The body skin is thus relieved in the contact regions.

The adhesive composition may be applied on the outer wall area 50a of the adapter type molding 50; alternatively it is possible to integrate the adhesive composition in the molding 50, as is indicated at 151 in FIG. 5.

In order additionally to strengthen the breast prostheses of the invention at their contact region and to protect them against tearing, a textile insert (not shown), for example of high-strength polyamide threads, may be inserted in the contact area 16. Preferably the textile insert is covered on the contact area side by a synthetic layer.

When needed, i.e., when it is for example temporarily more comfortable for the wearer not to do a gluing on the skin, the breast prostheses may be worn also without the adapter type molding as insert in the bra. The annular groove type section 18 is then advantageous inasmuch as it facilitates as natural as possible a swinging with the breast prosthesis, in particular of the gel body 30.

Other advantages and realizations of the invention will become evident from the claims which follow.

We claim:

1. Breast prosthesis of an elastic plastic, in particular of the silicone rubber composition, having a breast molding corresponding to the female breast and having a bearing surface adapted to conform to the human body form, and on which an adhesive is applied for attachment of the breast prosthesis to the body, characterized in that the upper portion of the breast molding is in the form of a cup having an approximately centered recess in the direction of the body, in combination with an adapter type molding retained in said recess, said cup being rotatable about said molding on its vertical median axis, and in which the external wall area of said molding, turned toward the body, is provided with a coating of an adhesive composition tolerated by the skin.

2. Breast prosthesis according to claim 1 in which the recess in the breast molding is cylindrical and is formed about its inner wall with an annular guide profile, and in which said adapter type molding is disk-shaped with a counter-profile integrally formed about its peripheral wall and is engagingly retained by the annular guide profile of said recess.

3. Breast prosthesis according to claim 2, in which the said recess is formed with an annular wall section leading into the bearing surface of the breast molding, to which wall section an annular groove type section is contiguous, while the adapter type molding comprises at its peripheral wall a counter-profile engaging the annular profile formed by the annular wall section and the annular groove type.

4. Breast prosthesis according to claims 1, 2 or 3 in combination with a detachable protective sheet covering the said coating of adhesive composition.

5. Breast prosthesis according to claim 1, in which said breast molding has in its upper part, in particular its nipple region, a soft core which is highly flexible relative to the material of said cup.

6. Breast prosthesis according to claim 5, in which said highly flexible soft core is formed in the upper front portion of the breast molding.

7. Breast prosthesis according to claims 5 or 6, in which the highly flexible soft core extends into the lower portion of the breast molding adjacent said adapter type molding.

8. Breast prosthesis according to claim 7 in which for the formation of the soft core the breast molding has in its upper part in its nipple region an upper wall section formed as a thin skin, and in its lower portion a lower wall section formed as a thin skin, the said two wall sections being connected together to form a bladder type closed cavity containing a silicone gel body.

9. Breast prosthesis according to claim 8, in which the walls of the breast molding laterally limiting the silicone gel body are formed tapering uniformly and conically toward the upper part thereof.

10. Breast prosthesis according to claim 9 in which the silicone gel body and the skin type walls of the breast molding are formed to mutually integrate in their contact regions during a vulcanization process.

11. Breast prosthesis according to claim 8, in which the wall area of the breast molding limiting the cavity is internally lined with a foil preventing penetration of the silicone gel body components through the cup.

12. Breast prosthesis according to claim 7 in which the said adapter type molding is provided in the region of its upper wall with a soft core of highly flexible material relative to the other molding material.

* * * * *